United States Patent
Kempf et al.

(10) Patent No.: US 7,320,961 B2
(45) Date of Patent: Jan. 22, 2008

(54) METHOD FOR TREATING A DISEASE, DISORDER OR ADVERSE EFFECT CAUSED BY AN ELEVATED SERUM CONCENTRATION OF AN UGT1A1 SUBSTRATE

(75) Inventors: Dale J. Kempf, Libertyville, IL (US); Richard J. Bertz, Kenosha, WI (US); Jeffrey F. Waring, Franklin, WI (US)

(73) Assignee: Abbott Laboratories, Abbott Park, IL (US)

( * ) Notice: Subject to any disclaimer, the term of this patent is extended or adjusted under 35 U.S.C. 154(b) by 246 days.

(21) Appl. No.: 10/802,829

(22) Filed: Mar. 18, 2004

(65) Prior Publication Data

US 2004/0242509 A1    Dec. 2, 2004

Related U.S. Application Data

(60) Provisional application No. 60/457,138, filed on Mar. 24, 2003.

(51) Int. Cl.
  *A61K 31/425*    (2006.01)
  *A61K 38/00*    (2006.01)
(52) U.S. Cl. .......................................... 514/19; 514/365
(58) Field of Classification Search ...................... None
  See application file for complete search history.

(56) References Cited

U.S. PATENT DOCUMENTS

| | | | |
|---|---|---|---|
| 6,037,157 A | 3/2000 | Norbeck et al. | |
| 2004/0192624 A1 | 9/2004 | Kempf et al. | 514/43 |

OTHER PUBLICATIONS

Agarwala et al., "Steady state pharmacokinetic (PK) interaction study of Atazanavir (ATV) with Ritonavir (RTV) in healthy subjects," Poster presented at the 42nd Interscience Conference on Antimicrobial Agents and Chemotherapy, San Diego, CA, Sep. 27-30th, 2002.
O'Mara et al., "Relationship between uridine diphosphate-glucuronsyl transferase (UDP-GT) 1A1 Genotype and total bilirubin elevations in healthy subjects receiving BMS-232632 and saquinavir," Poster presented at the 40th Interscience Conference on Antimicrobial Agents and Chemotherapy, Toronto, Ontario, Canada, Sep. 17-20, 2000.
Zucker et al., "Mechanism of indinavir-induced hyperbilirubinemia," PNAS 98(22):12671-12676 (2001).
Ritter, Joseph K., "Expression and inducibility of the human bilirubin UDP-glucuronosyltransferase UGT1A1 in liver and cultured primary hepatocytes: Evidence for both genetic and environmental influences", Hepatology, vol. 30, No. 2, Aug. 1999, pp. 476-484.
Sugatani, Junko, et al., "The Phenobarbital response enhancer module in the human bilirubin UDP-glucuronosyltransferase UGT1A1 gene and regulation by the nuclear HEPATOLOGY", vol. 33, No. 5, May 2001-05, pp. 1232-1238.
Baede, P., et al, "Drug interactions with TMC125, a potent next generation NNRTI", Abstracts of the Interscience Conference on Antimicrobial Agents and Chemotherapy, vol. 42, 2002, p. 27 & American Society for Microbiology (ASM) Annual Meeting on Infectious Disease; San Diego, CA, USA; Sep. 27-30, 2002 abstract.
Penzak, Scott, et al., "Influence of ritonavir on olanzapine pharmacokinetics in healthy volunteers", Journal of Clinical Psychopharmacology, vol. 22, No. 4, Aug. 2002, pp. 366-370.
Ouellet Daniele, et al, "Effect of ritonavir on the pharmacokinetics of ethinyl oestradiol in healthy female volunteers", British Journal of Clinical Pharmacology, vol. 46, No. 2, Aug. 1998, pp. 111-116.
O'Mara E. et al., "Steady state pharmacokinetic interaction study of atazanavir (ATV) with efavirenz (EFV) and ritonavir (RTV) in healthy subjects" Programs and abstracts of the 9th Conference on Retroviruses and Opportunistic Infections; Feb. 24-28, 2002, Seattle, Washington. Abstract 444.
A. Radominska-Pandya et al., *Structural and Functional Studies of UDP-Glucoronosyltransferases*, Drug Metabolism Reviews 31(4):817-99 (1999).
R.H. Tukey et al., *Human UDP-Glucoronosyltransferases: Metabolism, Expression, and Disease*, Ann. Rev. Pharmacol. Toxicol. 40:581-616 (2000).

Primary Examiner—Raymond J. Henley, III
(74) Attorney, Agent, or Firm—Michael J. Ward; Lydia Nenow

(57) ABSTRACT

The present invention is directed to a method for inducing UGT1A1 isoform expression for treatment of a disease, disorder or adverse effect caused by an elevated serum concentration of an UGT1A1 substrate comprising the step of administering to a subject an effective amount of ritonavir. In particular, the present invention is directed to a method of treating unconjugated hyperbilirubinemia by UGT1A1 induction comprising the step of administering to a subject an effective amount of ritonavir.

11 Claims, 6 Drawing Sheets

SEQUENCE LISTING

<160> NUMBER OF SEQ ID NOS: 1

<210> SEQ ID NO 1
<211> LENGTH: 63
<212> TYPE: DNA
<213> ORGANISM: Artificial
<220> FEATURE:
<223> OTHER INFORMATION: modified T7 primer (with 24 thymidines at the 3'-end)

<400> SEQUENCE: 1

```
ggccagtgaa ttgtaatacg actcactata gggaggcggt tttttttttt tttttttttt    60
ttt                                                                   63
```

METHOD FOR TREATING A DISEASE, DISORDER OR ADVERSE EFFECT CAUSED BY AN ELEVATED SERUM CONCENTRATION OF AN UGT1A1 SUBSTRATE

This application claims priority from U.S. Provisional Patent Application Ser. No. 60/457,138, filed Mar. 24, 2003, incorporated herein by reference.

FIELD OF THE INVENTION

The present invention is directed to a method for inducing UGT1A1 isoform expression for treatment of a disease or disorder or adverse effect caused by an elevated serum concentration of an UGT1A1 substrate comprising the step of administering to a subject an effective amount of ritonavir. In particular, the present invention is directed to a method of treating unconjugated hyperbilirubinemia by UGT1A1 induction comprising the step of administering to a subject an effective amount of ritonavir.

BACKGROUND OF THE INVENTION

Glucuronidation is a major metabolic pathway that determines the disposition of several endogenous substrates, such as for example, estriol and bilirubin, as well as exogenous substrates such as ethinylestradiol. The UDP-glucuronosyl-transferases (UGTs) are a superfamily of enzymes which catalyze these reactions with UDG-glucuronic acid as a cofactor. The UGT superfamily comprises at least ten isozymes in rat and more than ten isozymes in humans. In fact, a total of 15 human UGT isozymes have been identified each with distinct substrate specificities, UGT1A1 being a bilirubin-specific isozyme. Bilirubin is the principal product of heme catabolism, and is cleared from circulation by the liver where it undergoes glucuronidation, i.e., conjugation with glucuronic acid to form water-soluble metabolites such as mono- and diglucuronides which are ultimately excreted in the feces.

Indinavir (Merck & Co. Inc., New Jersey, USA) is a potent and commonly used protease inhibitor that has been shown to be highly effective against HIV when used in combination with reverse transcriptase inhibitors. Zucker, S. D., Qin. X, Rouster, S. D., et al. *Mechanism of indinavir-induced hyperbilirubinemia*, PNAS 2001; 98:12671–12676. Unfortunately, indinavir therapy is associated with a 6-25% incidence of asymptomatic, unconjugated hyperbilirubinemia in the absence of histologic liver injury. Id. Patients in whom excessive accumulation of bilirubin leads to the development of clinical jaundice have been subjected to treatment interruption and additional clinical investigation. Id. It has been found that elevations in serum-unconjugated bilirubin associated with indinavir treatment result from direct inhibition of bilirubin-conjugating activity. Id.

Similarly, Atazanavir (Bristol-Myers Squibb, New Jersey, USA) also causes an elevation in blood levels of unconjugated bilirubin. In one study, 57% of subjects taking atazanavir exhibited unconjugated hyperbilirubinemia. Agarwala, S., Russo, R., et al. *Steady State Pharmacokinetic (PK) Interaction Study of Atazanavir (ATV) with Ritonavir (RTV) in Healthy Subjects*, poster presented at the 42nd Interscience Conference on Antimicrobial Agents and Chemotherapy, San Diego, Calif., Sep. 27–30, 2002. It has been found that atazanavir in both an in vitro system of human microsomes and in human cells transfected with the UGT1A1 isoform inhibits bilirubin conjugation in the micromolar range. O'Mara, E., Mummaneni, V. et al. *Relationship Between Uridine Diphosphate-Glucuronosyl Transferase (UDP-GT) 1A1 Genotype and Total Bilirubin Elevations in Healthy Subjects Receiving BMS-232632 and Saquinavir*, poster presented at the 40th Interscience Conference on Antimicrobial Agents and Chemotherapy, Toronto, Ontario, Canada, Sep. 17–20, 2000.

Unconjugated hyperbilirubinemia is also an adverse effect associated with medicaments or combinations of medicaments such as, for example, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine.

In order to overcome a disease or disorder or adverse effect due to elevations in serum UGT1A1 substrates such as, for example, unconjugated hyperbilirubinemia it is desirable to induce UGT1A1.

It is also desirable to be able to treat HIV infection and AIDS with potent HIV protease inhibitors such as, for example, indinavir and atazanavir without having to discontinue treatment because of elevations in serum bilirubin caused by inhibition of UGT1A1.

Further, it is desirable to administer medicaments such as, for example, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine without having to discontinue treatment because of elevations in serum bilirubin.

SUMMARY OF THE INVENTION

The present invention provides a method for inducing UGT1A1 isoform expression for treatment of a disease or disorder or adverse effect caused by an elevated serum concentration of UGT1A1 substrates comprising the step of administering to a subject an effective amount of ritonavir. Preferably, the present invention provides a method for treating unconjugated hyperbilirubinemia comprising the step of administering an effective amount of ritonavir to a subject in need thereof. In one embodiment, the effective amount of ritonavir is in a range of about 25 to about 1200 mg daily.

BRIEF DESCRIPTION OF THE FIGURES

In the figures.

DETAILED DESCRIPTION OF THE PREFERRED EMBODIMENTS

Figure 1:
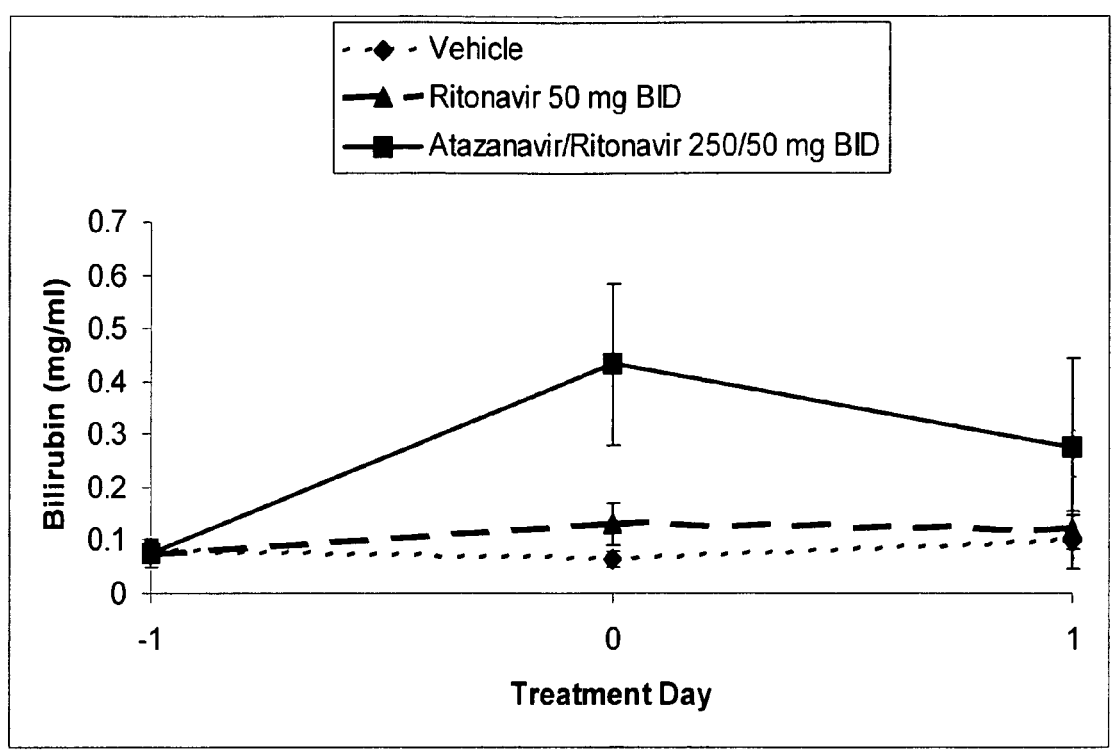
FIG. 1 shows the mean (±SD) serum bilirubin over time for the three groups of Gunn rats, wherein Group I received 500/100 mg/kg/day atazanavir/ritonavir, Group II received 100 mg/kg/day ritonavir, and Group III received only vehicle.

Surprisingly, it has been discovered that ritonavir induces UGT1A1 isoform expression. This is particularly useful in treatment of a disease or disorder or adverse effect caused by an elevated serum concentration of an UGT1A1 substrate. Unconjugated hyperbilirubinemia is an undesirable disease or disorder or adverse effect which is caused by administration to a subject of medicaments or combinations of medicaments such as, for example, indinavir, atazanavir, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine.

To overcome the undesirable disease or disorder or adverse effect, ritonavir can be co-administered with indinavir, atazanavir, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine to induce UGT1A1 isoform expression, and, in turn, lower serum bilirubin concentration.

In a first embodiment the present invention provides a method for inducing UGT1A1 for treatment of a disease or disorder or adverse effect caused by an elevated serum concentration of an UGT1A1 substrate comprising the step of administering to a subject an effective amount of ritonavir. Preferably, the present invention provides a method for treating unconjugated hyperbilirubinemia comprising the step of administering an effective amount of ritonavir to a subject in need thereof.

In a second embodiment the present invention provides a method for treating a disease or disorder or adverse effect caused by an elevated serum concentration of an UGT1A1 substrate upon administration of an active pharmaceutical ingredient comprising the step of co-administering ritonavir in an effective amount with the active pharmaceutical ingredient to a subject in need thereof. In one embodiment, the active pharmaceutical ingredient is selected from the group consisting essentially of indinavir, atazanavir, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine. In another embodiment, the active pharmaceutical ingredient is indinavir. In yet another embodiment, the active pharmaceutical ingredient is atazanavir. In one embodiment, the disease or disorder caused by an elevated serum concentration of an UGT1A1 substrate is unconjugated hyperbilirubinemia.

In a third embodiment, the present invention provides a method for increasing glucuronidation of an UGT1A1 substrate comprising the step of administering an effective amount of ritonavir. In one embodiment, the UGT1A1 substrate is bilirubin.

In a fourth embodiment, the present invention provides a method for increasing excretion of an UGT1A1 substrate comprising the step of administering an effective amount of ritonavir. In one embodiment, the UGT1A1 substrate is bilirubin.

In a fifth embodiment, the present invention provides a method for inducing UGT1A1 for treatment of a disease or disorder or adverse effect caused by an elevated serum concentration of an UGT1A1 substrate comprising the step of administering to a subject a composition comprising an effective amount of ritonavir. Preferably, the present invention provides a method for treating unconjugated hyperbilirubinemia comprising the step of administering a composition comprising an effective amount of ritonavir to a subject in need thereof. The composition may further comprise an effective amount of lopinavir in addition to the ritonavir. Examples of such a composition is disclosed in U.S. Pat. No. 6,458,818.

The terms "co-administration" and "co-adminstering" refer to administering to a subject ritonavir and another active pharmaceutical ingredient as separate dosage forms which are administered at same or different times, or together as a single dosage form.

The term "subject" refers to a mammal, and, more particularly to a human.

The phrase "effective amount" is an amount of ritonavir which is sufficient to induce UGT1A1 isoform expression or to increase glucuronidation of an UGT1A1 substrate or to increase excretion of an UGT1A1 substrate. In a preferred embodiment, the effective amount of ritonavir is an amount in a range of about 25 mg to about 1200 mg daily.

The amount of ritonavir that may be combined with carrier materials to produce a single dosage form will vary depending upon the subject treated and the particular mode of administration.

It will be understood, however, that the specific dose level for any particular subject will depend upon a variety of factors including a subject's age, body weight, general health, sex and diet, as well as time of administration, route of administration, rate of excretion, drug combination, and severity of a disease or disorder or adverse effect caused by an elevation of serum bilirubin.

Ritonavir is represented structurally as formula (I) below.

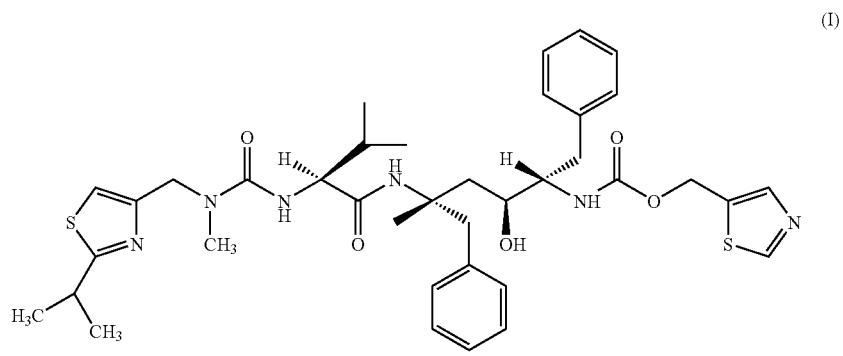

(I)

Ritonavir can be prepared using any of the procedures disclosed in U.S. Pat. Nos. 5,142,056, 5,151,438, 5,354,866, 5,362,912, 5,491,253, 5,508,409, 5,526,677, 5,539,122, 5,541,206, 5,541,328, 5,541,334, 5,543,549, 5,543,551, 5,543,552, 5,545,750, 5,552,558, 5,554,783, 5,565,418, 5,565,604, 5,567,823, 5,569,777, 5,580,984, 5,583,232, 5,583,233, 5,591,860, 5,597,926, 5,597,927, 5,597,928, 5,608,072, 5,616,714, 5,616,720, 5,616,776, 5,625,072, 5,625,092, 5,635,523, 5,648,497, 5,654,466, 5,659,044, 5,659,045, 5,670,675, 5,674,882, 5,679,797, 5,696,270, 5,786,500, 5,837,873, 5,846,987, 5,886,036, 5,892,052, 6,017,928, 6,150,530 and 6,531,610 which are incorporated in their entirety herein by reference.

Ritonavir is also known to be an HIV protease inhibitor and an inhibitor of cytochrome P450 monooxygenase, especially, CYP3A4 as disclosed in U.S. Pat. No. 6,037,157.

Ritonavir may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrastemal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of ritonavir can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, ritonavir may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Ritonavir can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically aceptable and metabolizable lipid capabale of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed. Methods in Cell Biology, Volume XIV, Academic Press, New York, N.Y. (1976), p. 33 et seq.

Examplary ritonavir formulations are disclosed in U.S. Pat. Nos. 5,142,056, 5,151,438, 5,354,866, 5,362,912, 5,484,801, 5,491,253, 5,508,409, 5,526,677, 5,539,122, 5,541,206, 5,541,328, 5,541,334, 5,543,549, 5,543,551, 5,543,552, 5,545,750, 5,552,558, 5,554,783, 5,559,158, 5,565,418, 5,565,604, 5,567,823, 5,569,777, 5,580,984, 5,583,232, 5,583,233, 5,591,860, 5,597,926, 5,597,927, 5,597,928, 5,608,072, 5,610,193, 5,616,714, 5,616,720, 5,616,776, 5,625,072, 5,625,092, 5,635,523, 5,648,497, 5,654,466, 5,659,044, 5,659,045, 5,670,675, 5,674,882, 5,679,797, 5,696,270, 5,725,878, 5,786,500, 5,837,873, 5,846,987, 5,876,749, 5,886,036, 5,892,052, 5,948,436, 6,017,928, 6,150,530, 6,232,333, 6,458,818, 6,521,651, and 6,531,610, published U.S. Patent Application No. US-2003-0032619-A1 and published PCT Application Nos. WO 93/23361, WO 94/14436, WO 95/07696, WO 95/09614, WO 95/20384, WO 98/22106, WO 00/74677, WO 01/52821 and WO 02/096395 which are incorporated in their entirety herein by reference. It should be noted that while the aforementioned references disclose various ritonavir formulations as examples, the present invention is not limited thereto.

The following examples will serve to further illustrate UGT1A1 induction by ritonavir.

EXAMPLE 1

Atazanavir/ritonavir were co-administered to Gunn rats (n=8) which are deficient for UDP-glucuronosyltransferase (UGT) activity by gavage at a total daily dosage of 500/100 mg/kg/day. A second set of rats received ritonavir at a total daily dosage of 100 mg/kg/day. A third group of rats was administered vehicle only. Atazanavir was formulated in a vehicle consisting of 5% EtOH:95% propylene glycol (PG):1 molar equivalent of p-toluene sulfonic acid. Ritonavir was formulated in a vehicle consisting of 5% EtOH:95% propylene glycol (PG):2 molar equivalents of p-toluene sulfonic acid. Formulations were prepared so that all rats received a total constant volume of 2 ml/kg with each treatment. Rats were dosed twice daily on Day 0 approximately twelve hours apart, and a third time in the morning on Day 1, for a total of three doses.

A sample of blood (approximately 0.5 ml) was collected from each rat via the jugular vein into a plain microcentrifuge tube (no anticoagulant) 4 hours following the first and third dose, and used for analysis of total bilirubin. The mean (±SD) serum bilirubin over time for the three groups of rats is shown in FIG. 1. Serum bilirubin markedly increased after the first dose, then declined after three doses.

Figure 2:
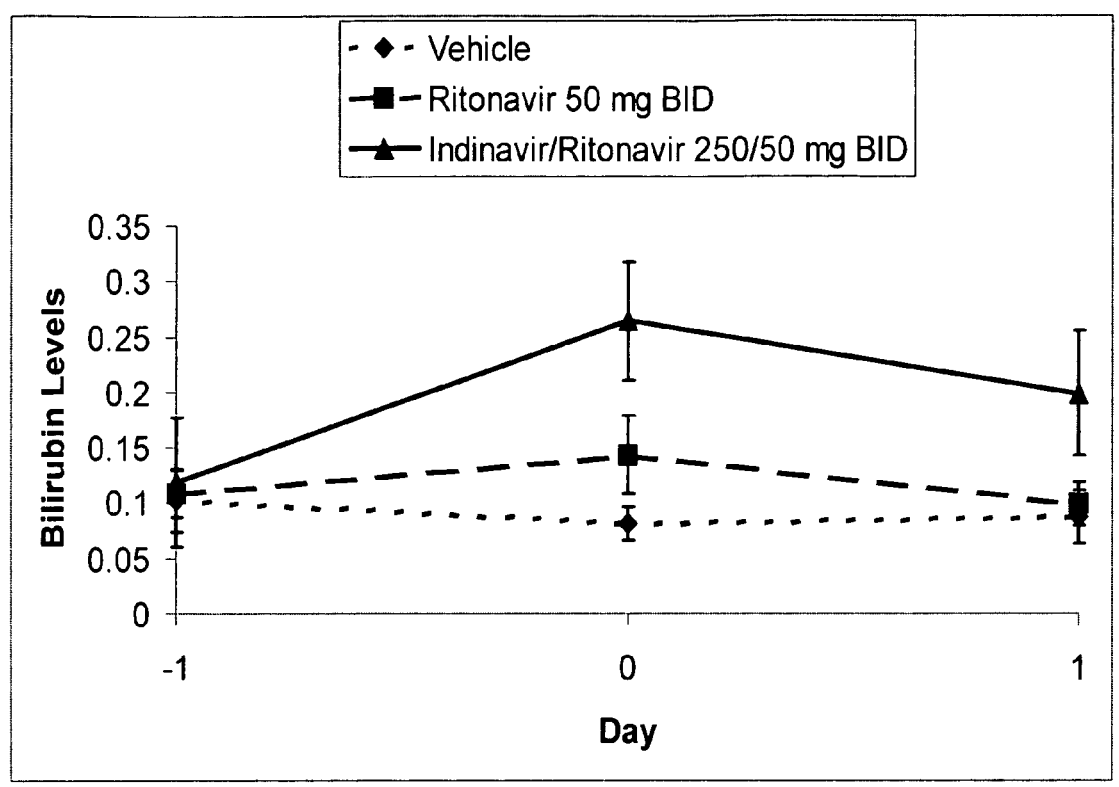
FIG. 2 shows the mean (±SD) serum bilirubin over time for the three groups of Gunn rats, wherein Group I received 500/100 mg/kg/day indinavir/ritonavir, Group II received 100 mg/kg/day ritonavir, and Group III received only vehicle.

The same procedure was used to evaluate the bilirubin elevations produced by indinavir/ritonavir, and the results are shown in FIG. 2. Again, serum bilirubin markedly increased after the first dose, then declined after three doses.

EXAMPLE 2

Male Sprague-Dawley rats approximately 6–12 weeks of age and weighing between 225 and 275 grams were dosed orally with ritonavir at the indicated concentrations. Ritonavir was formulated in 5% ethanol:95% propylene glycol:2 molar equivalents of p-toluene sulfonic acid. The rats were dosed daily for one or three days, and were sacrificed on the following day. Approximately 100 mg from each liver was placed into TRizol® reagent, and immediately homogenized using a Turrax tissue grinder.

RNA preparation and analysis was done according to the Affymetrix Inc. protocol. The integrity of the RNA from the pooled samples was determined using an Agilent 2100 Bioanalyzer. cDNA was prepared from 15 ug of RNA using the Superscript Choice system from Gibco BRL Life Technologies (Cat. No. 18090-019). The Gibco protocol was followed exactly, with the exception that the primer used for the reverse transcription reaction was a modified T7 primer with 24 thymidines at the 3' end. The sequence was:
5'-GGCCAGTGAATTGTAATACGACTCAC-
TATAGGGAGGCGG-(dT)24-3' (SEQ ID NO:1).

Following this, labeled cRNA was synthesized from the cDNA using the Enzo RNA Transcript Labeling Kit (Cat. No. 900182) according to the manufacturer's instructions. Approximately 20 mg of cRNA was then fragmented in a solution of 40 mM Tris acetate, pH 8.1, 100 mM KOAc, and 30 mM MgOAc at 94o for 35 minutes. Following this, cRNA was hybridized to the Affymetrix Rat U34 Chip which contains approximately 9000 gene sequences. The cRNA was hybridized overnight at 45° C.

The microarray data was analyzed using the Rosetta Resolver v2.0 Expression Data Analysis System. Expression changes between two arrays were quantified as "fold change" where the expression ratio was taken to be the ratio between normalized, error-weighted PM/MM difference intensities.

The Affymetrix U34A chip contains 5 different probe sequences which correspond to UDP-glucuronosyltransferase 1A (UGT1A). The induction of these probe sets in response to ritonavir treatment is shown in Table I. Treatment of rats with ritonavir at dose levels of 100 mg/kg and higher showed a consistent increase in UGT1A levels for all probe sets after 1 and 3 days of treatment. The results indicate that ritonavir is an inducer of UGT1A expression.

TABLE 1

Induction of 5 different probe sequences in response to ritonavir treatment.

3-Day Studies

| 50 mg/kg Fold change | 50 mg/kg Fold change | 75 mg/kg Fold change | 100 mg/kg Fold change | 125 mg/kg Fold change | Sequence Description |
|---|---|---|---|---|---|
| ND | ND | 1.56 | 1.67 | 1.54 | UDP-glucuronosyltransferase 1 family, member 1 |
| ND | ND | 1.38 | 1.46 | 1.42 | UDP-glucuronosyltransferase 1 family, member 1 |
| 1.31 | 1.33 | 1.57 | 1.61 | 1.65 | UDP-glucuronosyltransferase 1 family, member 1 |
| 1.54 | 1.85 | 1.97 | 2.26 | 2.25 | 3-methylcholanthrene-inducible UDP-glucuronosyltransferase |
| ND | ND | ND | 3.96 | 5.06 | UDP glucuronosyltransferase, exon 1. |

1-Day Studies

| 20 mg/kg Fold change | 20 mg/kg Fold change | 50 mg/kg Fold change | 50 mg/kg Fold change | 175 mg/kg Fold change | Sequence Description |
|---|---|---|---|---|---|
| 1.63 | ND | 1.68 | 1.63 | 2.02 | UDP-glucuronosyltransferase 1 family, member 1 |

TABLE 1-continued

Induction of 5 different probe sequences in response to ritonavir treatment.

| | | | | | |
|---|---|---|---|---|---|
| 1.68 | 1.51 | 2.12 | 2.05 | 1.86 | UDP-glucuronosyltransferase 1 family, member 1 |
| 1.8 | 1.52 | 1.75 | 2.12 | 2.49 | UDP-glucuronosyltransferase 1 family, member 1 |
| 1.83 | 1.54 | 1.63 | 2.1 | 2.8 | 3-methylcholanthrene-inducible UDP-glucuronosyltransferase |
| ND | ND | ND | 2.43 | ND | UDP glucuronosyltransferase, exon 1. |

ND = Not Detected

EXAMPLE 3

Ritonavir was prepared as 7.5 and 25 mg/mL solutions in 5% ethanol, 95% propylene glycol and 2 molar equivalents of p-toluenesulfonic acid. Rats in the control group received vehicle consisting of 5% ethanol, 95% propylene glycol and 37.6 mg/mL p-toluenesulfonic acid. Sodium phenobarbital dose solution was prepared in normal saline at a concentration of 25 mg base/ml.

Sixteen male and female Sprague-Dawley rats (VAF Crl:CD@ (SD)BR) weighing about 250 g were obtained from Charles River Laboratories, Inc. (Portage, Mich.). The rats were randomly divided into four treatment groups shown in Table 2.

TABLE 2

Therapies received by Treatment Groups $T_0$, $T_1$, $T_2$ and $T_3$

| TREATMENT GROUP | NUMBER OF RATS MALE | FEMALE | DRUG | DOSAGE MG/KG | DURATION (DAYS) |
|---|---|---|---|---|---|
| $T_0$ | 4 | 4 | Vehicle | 0 | 14 |
| $T_1$ | 4 | 4 | Ritonavir | 15 | 14 |
| $T_2$ | 4 | 4 | Ritonavir | 50 | 14 |
| $T_3$ | 4 | 4 | Phenobarbitol | 50 | 4 |

The animals were given free access to Certified Rodent Chow* #5002 pellets (Purina Mills, Inc., St. Louis, Mo.) and water. The rats were housed individually in stainless steel cages and were identified by a unique identifier number. Body weights were recorded on Day 0, Day 7 and at the end of the study.

Each rat in treatment groups $T_0$, $T_1$, and $T_2$ received an oral dose, by gavage, of ritonavir at a constant dose volume of 2 mL/kg once each day for fourteen consecutive days. Each rat in treatment Group $T_3$ received an intraperitoneal dose of phenobarbital at a constant dose volume of 2 mL/kg, once daily, for four consecutive days.

The rats in treatment Groups $T_0$, $T_1$ and $T_2$ were sacrificed at approximately 48 hours after the last dose. The rats in treatment Group $T_3$ were sacrificed at approximately 24 hours after the last dose. The livers were removed, blotted dry and weighed individually. The livers were then homogenized individually in ice-cold 1.15% potassium chloride containing 10 mM potassium phosphate buffer (pH 7.4) using a tissue homogenizer. Microsomes were prepared by differential centrifugation and were stored at −70° C. in 0.1 M potassium phosphate buffer (pH 7.4) containing 20% (v/v) glycerol and 1.0 mM EDTA. Microsomal protein content was determined using a bicinchoninic acid (BCA) assay kit (Pierce Chemical), with bovine serum albumin as the standard. Total cytochrome P450 content was determined by means of ferrous carbon monoxide complex formation. The microsomes were characterized for the following cytochrome P450-mediated reactions: 7-pentoxyresorufin O-dealkylase, chlorzoxazone 6-hydroxylase, benzphetamine N-demethylase and erythromycin N-demethylase.

Hepatic 17α-ethinylestradiol and 1-naphthol glucuronidation activities are summarized in Table 3 below.

TABLE 3

17α-ethinylestradiol and 1-naphthol glucuronidation activities for Treatment Groups $T_0$, $T_1$, $T_2$ and $T_3$.

| Treatment Group | 17α-ethinylestradiol glucuronidation (pmol/mg/min) | | 1-naphthol glucuronidation (nmol/mg/min) | |
|---|---|---|---|---|
| | 100 μM | 250 μM | 50 μM | 1000 μM |
| Males | | | | |
| $T_0$ | 28.9 ± 7.5 | 143.0 ± 33.3 | 9.1 ± 1.0 | 19.5 ± 3.7 |
| $T_1$ | 58.8 ± 2.2 | 171.8 ± 38.1 | 9.5 ± 1.5 | 23.0 ± 2.5 |
| $T_2$ | 34.0 ± 10.0 | 290.1 ± 45.6 | 8.3 ± 1.4 | 22.8 ± 4.3 |
| $T_3$ | 45.1 ± 16.5 | 258.5 ± 98.5 | 15.4 ± 3.1 | 41.0 ± 5.0 |
| Females | | | | |
| $T_0$ | 39.6 ± 12.7 | 278.0 ± 78.3 | 5.5 ± 0.8 | 29.4 ± 2.3 |
| $T_1$ | 54.5 ± 24.0 | 336.4 ± 75.8 | 7.3 ± 1.2 | 33.7 ± 5.2 |
| $T_2$ | 146.5 ± 26.0 | 590.9 ± 101.2 | 10.0 ± 2.7 | 37.7 ± 4.9 |
| $T_3$ | 91.0 ± 34.0 | 360.6 ± 88.1 | 9.3 ± 0.4 | 46.4 ± 8.6 |

Ritonavir was found to significantly increase the glucuronidation of 17α-ethinylestradiol, a UGT1A1 substrate, in both male and female rats. The increase in glucuronidation of 17α-ethinylestradiol was 2-fold in both male and female rats treated with 50 mg/kg/day of ritonavir.

EXAMPLE 4

A study was conducted to investigate the effects of 500 mg oral ritonavir administered every 12 hours on the pharmacokinetics of a single dose of ethinylestradiol. This was an open-label, single-center study in healthy female volunteers who had not received an oral contraceptive for a minimum of six months prior to study start. Subjects received the first dose of oral contraceptive containing 50 μg of ethinyl estradiol on Day 1. Each subject received 16 days of q12h doses of ritonavir from Day 15 to Day 30. On Day 15, 300 mg q12h was administered, 400 mg q12h was given on Day 16, and 500 mg q12h was administered thereafter. The second dose of oral contraceptive was administered during ritonavir dosing, on Day 29. Blood samples for ethinylestradiol concentrations were collected for 48 h after each of the oral contraceptive doses. Blood samples for ritonavir concentrations were collected at baseline, i.e., prior to dosing on Day 1 (0 h), and at steady state on Day 29, at 0 and 4 h after the morning dose.

Twenty-seven subjects were enrolled in the study. Four subjects failed to complete the study and did not receive the oral contraceptive dose administered during ritonavir dosing. Data from these four subjects were therefore excluded from summary statistics. The mean ±SD age of the 23 subjects who completed the study was 34±10 yrs (range 19 to 45 yrs), the mean ±SD weight was 67.3±10.9 kg (range 50.8 to 90.3 kg), and the mean ±SD height was 167±7 cm (range 155 to 180 cm).

Ethinylestradiol was supplied as Demulen@ 1/50-21 tablets (G.D. Searle & Co.) containing 50 µg of ethinylestradiol and 1 mg of ethynodiol diacetate and was administered at 8:00 a.m. on Day 1 and Day 29 with approximately 240 mL of water and within 15 minutes of a meal or snack. Ritonavir (Abbott Laboratories) was supplied as a liquid formulation (80 mg/mL solution) and was administered as 300 mg (3.75 mL) every 12 hours on Day 15, 400 mg (5.0 mL) every 12 hours on Day 16, and 500 mg (6.25 mL) every 12 hours on Days 17 to 30, at approximately 8:00 a.m. and 8:00 p.m. on Days 15 to 30.

Subjects were confined for 64 hours from Day-1 (day prior to the initial dose) through the first 48 hour blood collection (morning of Day 3) and for 64 hours from Day 28 through the second 48 hour blood collection (morning of Day 31). In addition, subjects came to the clinical testing unit as outpatients for meals, dosing and other study activities twice daily for a total of 14 consecutive days, starting on Day 15. Strenuous activity during confinement was not permitted. During confinement, subjects abstained from all food and beverages except for the scheduled meals and snacks provided in the study. Water was available ad libitum. All meals were standardized with regard to content during confinement. Breakfast, lunch, and dinner were served at approximately 7:30 a.m., 1:00 p.m. and 7:30 p.m. and snacks were provided at approximately 10:00 p.m., except on Days-1 and 28 when the snack was served at 9:45 p.m. An 8 hour fast was required prior to all blood collections for clinical laboratory analyses. The sequence of starting breakfast and dinner on each dosing day during confinement was maintained to the minute such that the time intervals relative to dosing were the same among all subjects.

Blood samples (7 mL) were collected for serum ethinyl estradiol concentrations at the following times relative to the dose on Day 1 and Day 29: prior to (0 h) and at 0.5, 1, 2, 3, 4, 6, 8, 10, 12, 18, 24, 30, 36, and 48 h post-dose. In addition, blood samples (7 mL) were collected for plasma ritonavir concentrations prior to dosing on Day 1 (0 h) and at steady state on Day 29, at 0 h (prior to morning dosing) and 4 h after the morning dose. All plasma and serum samples were packed with dry ice and shipped to the analytical sites.

Serum samples were analyzed for ethinylestradiol concentrations at Pharmaco LSR, Richmond, Va. Plasma samples were stored frozen until analyzed for ritonavir concentrations at Oneida Research Services (ORS), Inc., Whitesboro, N.Y.

Analysis of serum samples for determination of ethinyl estradiol was performed at Pharmaco LSR, Richmond, Va. Ethinylestradiol serum concentrations were determined using a gas chromatography/mass spectrometry (GC/MS) method. 17α-ethinylestradiol and its corresponding isotopically labeled internal standard were isolated from human serum by buffering the serum to pH 8.6 and then extracting with an ethyl ether/methylene chloride mixture. The organic layer was exchanged into aqueous base, washed with hexane and then acidified and extracted with methylene chloride. The extract was dried with sodium carbonate, evaporated and derivatized. The derivatized extract was stored at −20° C. until analysis. Analysis was by capillary GC/MS using negative chemical ionization with selected ion monitoring. This method has been validated over 17α-ethinylestradiol concentrations ranging from 2.00 to 256 pg/mL for a 1.0 mL serum volume, with a minimum quantitation limit of 2.00 pg/mL.

The serum samples of the study were assayed with 17α-ethinylestradiol calibration curves ranging from 2.00 to 256 pg/mL and the mean correlation coefficient was 0.9994. As a quality control measure and a gauge of interassay variability, serum samples were supplemented with low, medium and high concentrations of ethinyl estradiol, and were assayed with the unknowns. The low, medium and high quality controls were 6.00, 24.0 and 144 pg/mL, respectively. The mean calculated concentration values for ethinylestradiol at the end of the analyses were 5.31, 21.4 and 131 pg/mL for the low, medium and high quality controls, respectively. The corresponding coefficients of variation were 11.4, 8.1 and 7.1%.

Analysis of ritonavir plasma samples was conducted at ORS, Whitesboro, N.Y. Ritonavir plasma concentrations were determined using a validated reverse-phase high performance liquid chromatographic (HPLC) method with UV detection. The extraction procedure involved the addition of an internal standard to a 500 µL aliquot of sample, extraction of this aliquot under neutral conditions with ethyl acetate: hexane; 9:1 (v/v), evaporation of the organic phase to dryness, and reconstitution of the sample in mobile phase, followed by two washes of the reconstituted extract with hexane. An aliquot of the reconstituted extract was then analyzed by reverse phase high performance liquid chromatography with ultraviolet detection at 205 nm. The lower limit of quantitation was 0.010 µg/mL. The mobile phase consisted of 0.1% trifluoroacetic acid (TFA) in 0.01 M tetramethylammonium perchlorate:acetonitile:methanol (55:40:5; v:v:v).

The procedure was validated at ORS and had been shown to produce linear calibration curves in plasma. The mean correlation coefficient for calibration curves with standards ranging from 0.100 to 15.00 µg/mL was 0.998. The within-day coefficients of variation (CVs) were below 4.85% at all concentrations. The inter-day CVs for plasma were below 5.66% at all concentrations.

An abbreviated validation was performed to demonstrate a lower limit of quantitation of 0.010 µg/mL in non-HIV positive plasma. Within-day CVs were 19.29% or less for all but the lowest concentration calibration standard which had a CV of 39.70% and the correlation coefficient for the calibration curve was 0.9960. Intra-assay variability obtained previously following the analysis of plasma containing 0.010 µg/mL of ritonavir in replicates of six demonstrated assay precision at the lower limit of quantitation of 4.25%.

The plasma samples of the study were assayed with calibration curves ranging from 0.010 to 15.00 µg/mL and the mean correlation coefficient was 0.9993. As a quality control measure and a gauge of interassay variability, plasma samples were supplemented with low (0.150 µg/mL), medium (7.500 µg/mL) and high (12.00 µg/mL) concentrations of ritonavir, and were assayed with the unknowns. The mean calculated concentration values at the end of the analyses were 0.158, 6.511 and 10.64 µg/mL and the corresponding coefficients of variation were 3.99, 12.9 and 2.88%, for the low, medium and high quality controls, respectively.

Ethinylestradiol pharmacokinetic parameters were estimated following two single doses, on Day 1 and Day 29, using noncompartmental methods. The pharmacokinetic parameters were calculated using the intended sampling times; all samples were collected within 10% of intended sampling times. Maximal plasma concentration (Cmax,) and time to reach Cmax (Tmax) were obtained directly from individual concentration vs. time profiles. The area under the plasma concentration-time curve (AUC∞) was calculated as the sum of AUCt, the area up to the last measurable concentration computed using the linear trapezoidal rule, and the extrapolation to infinity, calculated as the quotient of the last measurable concentration (Ct) and the terminal elimination rate constant ($\beta$). The terminal elimination rate constant was calculated as the negative of the slope of the regression of the logarithms of the plasma concentrations vs. time, starting at 18 h post-dose. The half-life of the terminal phase (t1/2) was obtained by dividing the natural logarithm of 2 (ln 2) by $\beta$.

Two ethinylestradiol concentrations were reported as missing and were replaced by linear interpolation (Subject No. 101 at 6 h on Day 29 and Subject No. 124 at 4 h on Day 29). One ritonavir concentration was reported as missing (Subject No. 124 at 4 h on Day 29) and was not replaced.

Serum concentrations of ethinylestradiol and plasma concentrations of ritonavir for each time of sampling were tabulated and summary statistics computed. Ethinylestradiol pharmacokinetic parameters (Tmax, Cmax, AUC∞ and $\beta$) measured on Day 1, when the oral contraceptive was administered alone, were compared to those obtained on Day 29, when the oral contraceptive was administered during concomitant ritonavir dosing, using a paired t-test on the difference. The paired t-test was performed using PROC UNIVARIATE of SAS version 6.09 on a UNIX operating system. A p value ≦0.050 was considered statistically significant.

For both Cmax and AUC∞, a 95% confidence interval was obtained for the ratio of the mean on Day 29, when the oral contraceptive was administered during concomitant ritonavir dosing, to the mean on Day 1, when the oral contraceptive was administered alone.

The relationships between the ethinylestradiol AUC ratio (Day 29:Day 1) and ritonavir concentrations on Day 29, and between ethinylestradiol AUC ratio (Day 29:Day 1) and natural logarithm (ln) transformed triglyceride ratios (Day 28:Day-1) or ln transformed gamma-glutamyl transpeptidase (GGT) ratios (Day 28:Day-1) were explored by simple linear regression analysis.

A summary of the results is listed in the table below for the ethinyl estradiol pharmacokinetic parameter estimates determined after administration of the oral contraceptive alone and after two weeks of q12h ritonavir.

TABLE 4

Ethinylestradiol pharmacokinetic parameters (Mean ± SD, n = 23) after administration of ethinylestradiol alone and with ritonavir

| Parameter | Ethinylestradiol | Ethinylestradiol plus Ritonavir | Ratio of Means | 95% CI for Ratio of Means |
|---|---|---|---|---|
| Tmax (hrs) | 4.0 ± 1.7 | 3.6 ± 1.3 | — | — |
| Cmax (pg/mL) | 104 ± 24 | 70.7 ± 18.1 | 0.682 | 0.612–0.758 |
| AUC∞ (pg · hr/mL) | 1670 ± 377 | 993 ± 292 | 0.595 | 0.506–0.694 |
| $\beta$ (hr$^{-1}$) | 0.0407 ± 0.0082 | 0.0535 ± 0.0139 | — | — |
| t$_{1/2}$ (hr)* | 17.0 | 13.0 | — | — |

*reported as harmonic mean.

Figure 3:
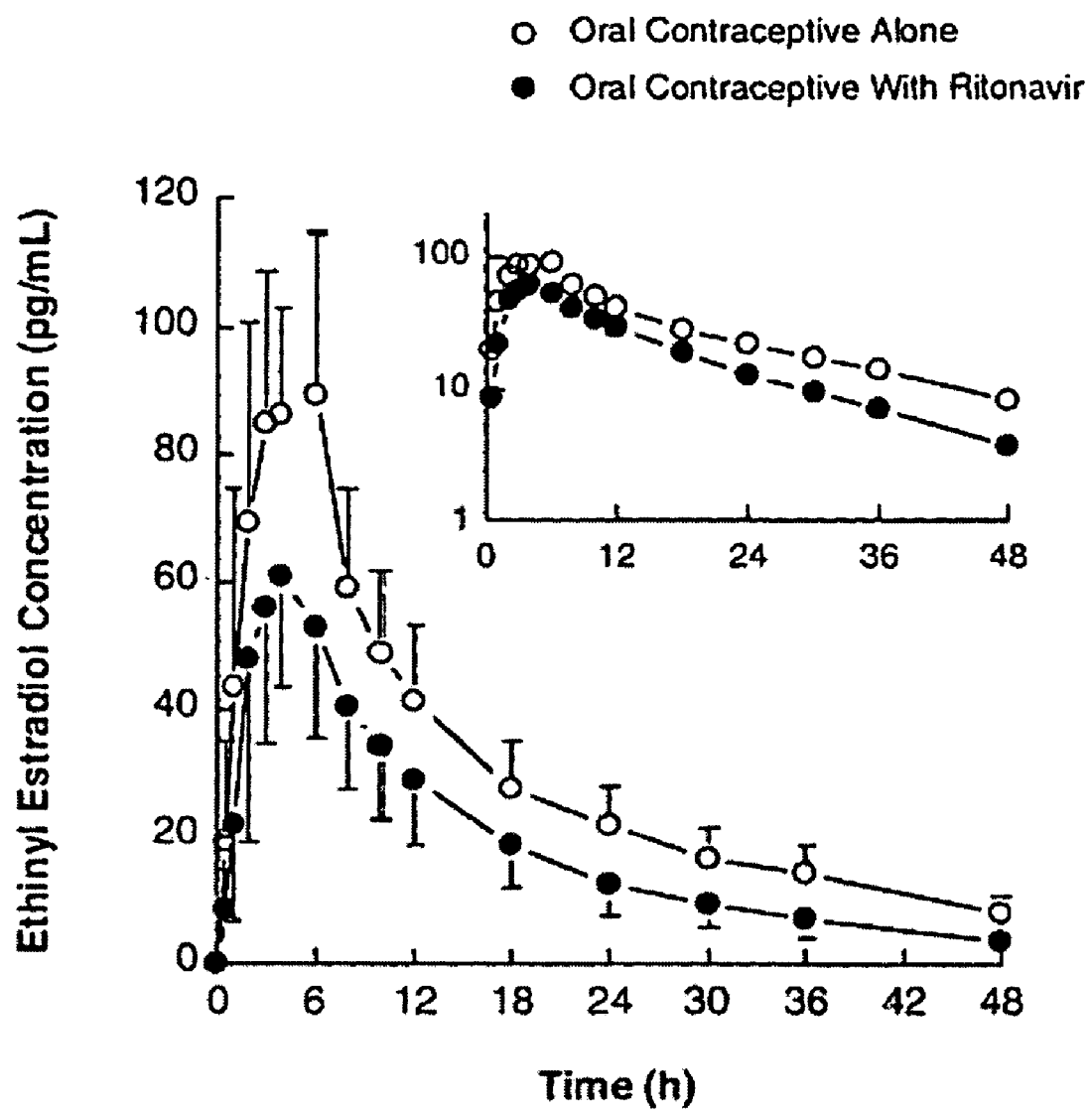
FIG. 3 shows mean (±SD) serum ethinylestradiol concentrations after administration of ethinylestradiol alone and with ritonavir.
Figure 4:
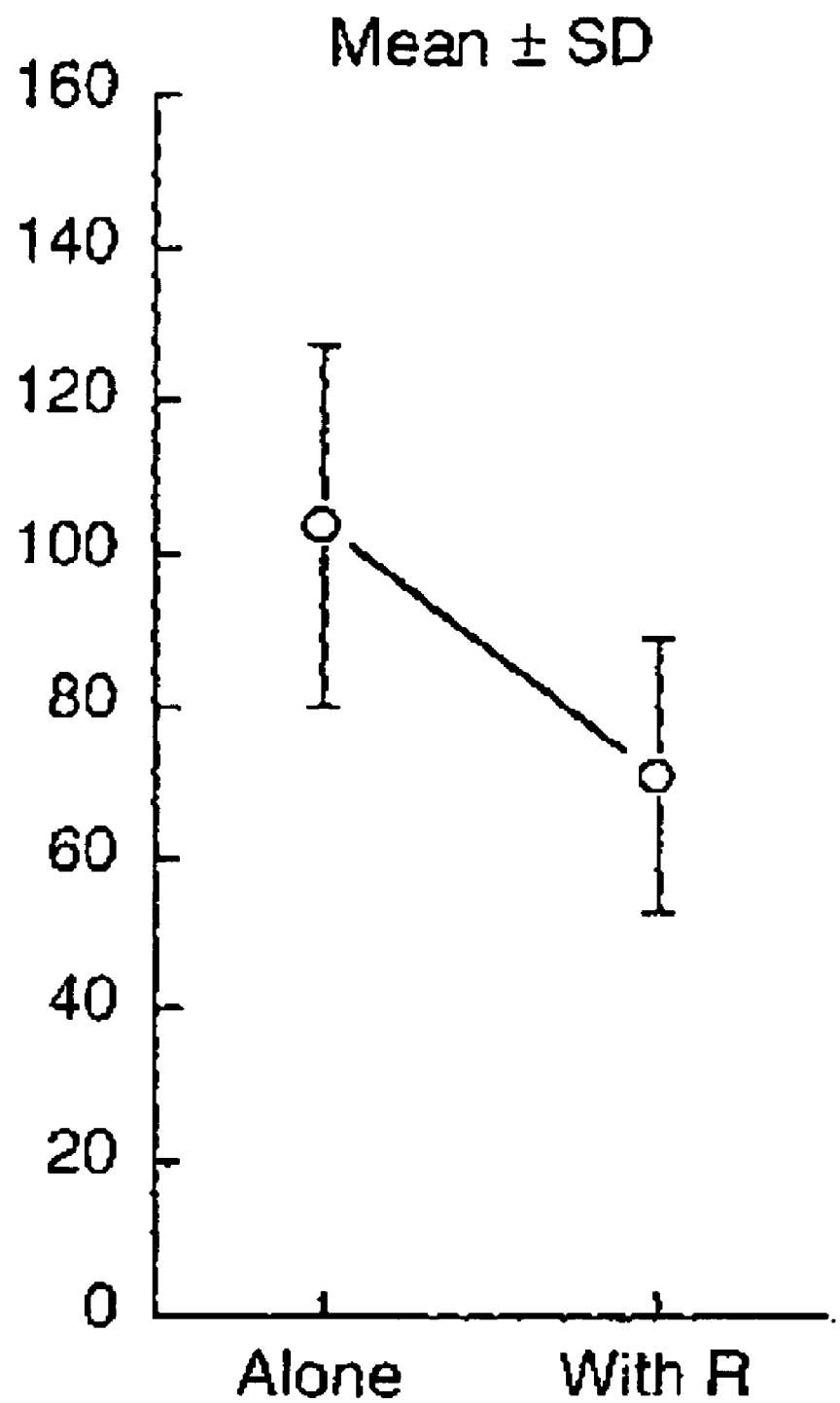
FIG. 4 shows individual and mean (±SD) ethinylestradiol Cmax after administration of ethinylestradiol alone and with ritonavir.
Figure 5:
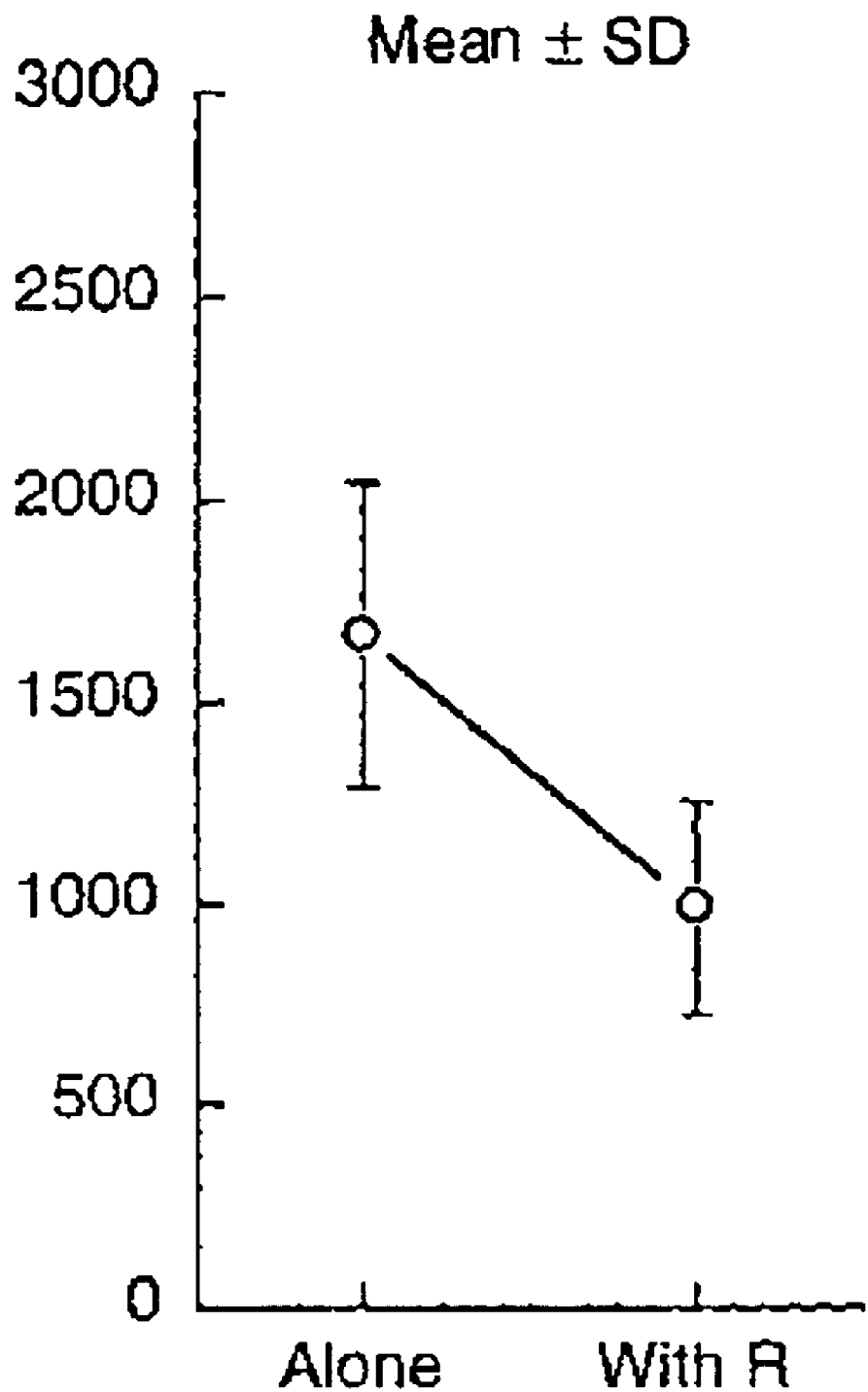
FIG. 5 shows individual and mean (±SD) ethinylestradiol AUC∞ after administration of ethinylestradiol alone and with ritonavir.
Figure 6:
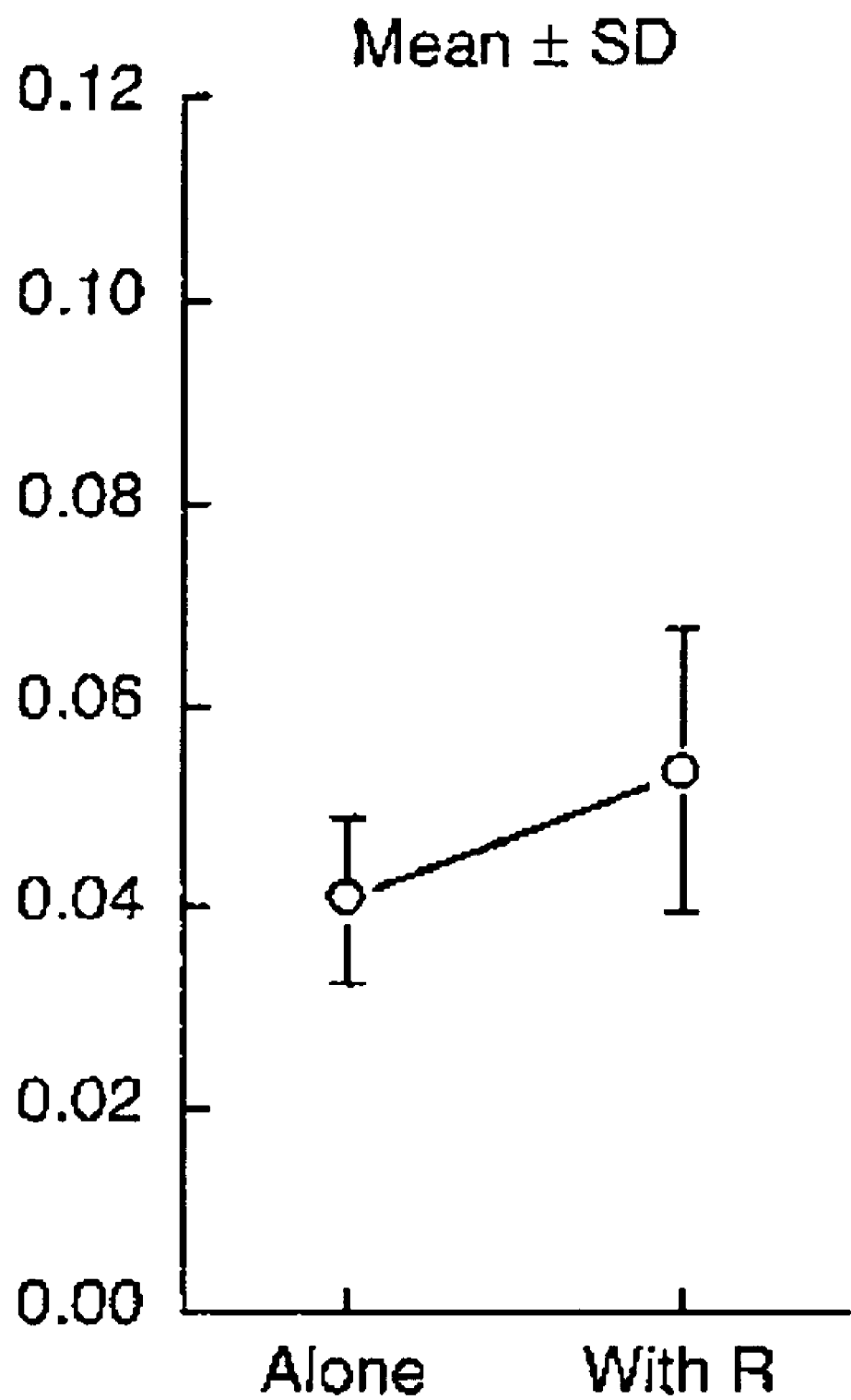
FIG. 6 shows individual and mean (±SD) ethinylestradiol elimination rate constant (β) after administration of ethinylestradiol alone and with ritonavir.

Following administration of a single dose of oral contraceptive, serum ethinylestradiol concentrations peaked at approximately 4 h post-dose and declined thereafter with a typical terminal elimination half-life of 17 h FIG. 3. The second dose of ethinylestradiol was given on Day 29, after approximately two weeks of 500 mg q12h ritonavir. Administration of ethinylestradiol with ritonavir resulted in 32% lower ethinylestradiol mean Cmax (p <0.001) and 41% lower mean AUC (p <0.001), compared to administration of the oral contraceptive alone. In addition, the mean terminal elimination rate constant increased by 31% (p <0.001) with concomitant ritonavir, with a harmonic mean half-life of 13 hours. Individual and mean changes in ethinylestradiol pharmacokinetic parameters after administration of the oral contraceptive alone and with ritonavir are presented in FIGS. 4–6, for Cmax, AUC and $\beta$, respectively.

The effect on AUC was consistent across individuals as is evident from the relatively narrow 95% confidence interval of the ratio of AUC means (0.506–0.694). All subjects except one had a decrease in AUC with ritonavir dosing. No statistically significant change was noted in Tmax (p=0.387).

Statistically significant differences were observed in ethinyl estradiol pharmacokinetic parameters determined after administration of the oral contraceptive alone and those determined during 500 mg q12h ritonavir administration, with the exception of Tmax. With ritonavir, ethinyl estradiol mean Cmax and mean AUC decreased by 32% and 41%, respectively, while an increase in the mean terminal elimination rate constant was observed (+31%). The harmonic mean half life of ethinyl estradiol decreased from 17.0 h after administration of the oral contraceptive alone to 13.0 h after administration of the oral contraceptive with ritonavir.

The foregoing is merely illustrative of the invention and is not intended to limit the invention to the disclosed methods and compositions. Variations and changes which are obvious to one skilled in the art are intended to be within the scope and nature of the invention which is defined in the appended claims.

What is claimed is:

1. A method for inducing UGT1A1 isoform expression for treatment of a disease, disorder or adverse effect caused by an elevated serum concentration of an UGT1A1 substrate comprising the step of administering to a subject an effective amount of ritonavir, wherein said elevated serum concentration of the UGT1A1 substrate is not caused by administration of atazanavir.

2. The method of claim 1 wherein the disease or disorder is unconjugated hyperbilirubinemia.

3. The method of claim 1 wherein the UGT1A1 substrate is bilirubin.

4. The method of claim 1 wherein the effective amount of ritonavir is in a range of about 25 to about 1200 mg daily.

5. A method for treating unconjugated hyperbilirubinemia comprising the step of administering an effective amount of ritonavir to a subject in need thereof, wherein said unconjugated hyperbilirubinemia is not caused by administration of atazanavir.

6. The method of claim 5 wherein the effective amount of ritonavir is in a range of about 25 to about 1200 mg daily.

7. A method for treating a disease, disorder or adverse effect caused by an elevated serum concentration of an UGT1A1 substrate comprising the step of administering ritonavir in an effective amount to a subject in need thereof, wherein said elevated serum concentration of the UGT 1 A1 substrate is not caused by administration of atazanavir.

8. The method of claim 7 wherein the effective amount of ritonavir is in a range of about 25 mg to about 1200 mg.

9. The method of claim 7, wherein said elevated serum concentration of the UGT1A1 substrate is a result of administration of an active pharmaceutical ingredient to the subject, and wherein the active pharmaceutical ingredient is selected from the group consisting of indinavir, amphotericin B/cholesteryl sulfate complex, testosterone, interferon beta-1b, bicalutamide, ciprofloxacin, oxaliplatin, floxuridine, gemcitabine hydrochloride, sargramostim, gemtuzumab ozogamicin, vinorelbine tartrate, carboplatin, peginterferon alfa-2B, tacrolimus, aldesleukin, dalfopristin/quinupristin, didanosine and capecitabine.

10. The method of claim 9 wherein the active pharmaceutical ingredient is indinavir.

11. The method of claim 7 wherein the disease, disorder or adverse effect caused by an elevated serum concentration of an UGT1A1 substrate is unconjugated hyperbilirubinemia.

* * * * *